United States Patent [19]

Aja

[11] Patent Number: 5,413,269
[45] Date of Patent: May 9, 1995

[54] METHOD TO IMPLANT DEFECTS IN A METALLIC COMPONENT

[75] Inventor: Juan A. D. Aja, San Touch, Spain

[73] Assignee: Equipos Nucleares, S.A., Spain

[21] Appl. No.: 994,217

[22] Filed: Dec. 18, 1992

[30] Foreign Application Priority Data

Dec. 18, 1991 [ES] Spain .................................. 9102811

[51] Int. Cl.⁶ .......................................... B23K 31/12
[52] U.S. Cl. ................................ 228/104; 73/866.4; 73/620; 228/170
[58] Field of Search ................. 228/103, 104, 170; 73/866.4, 1 DV, 620

[56] References Cited

U.S. PATENT DOCUMENTS

| | | | |
|---|---|---|---|
| 4,203,315 | 5/1980 | Vieu et al. | 73/1 DV |
| 4,309,904 | 1/1982 | Jones et al. | 73/1 DV |
| 4,343,424 | 8/1982 | Montemarano | 228/104 |
| 4,704,892 | 11/1987 | Tarnai | 73/1 DV |

FOREIGN PATENT DOCUMENTS

| | | | |
|---|---|---|---|
| 182733 | 7/1989 | Japan | 73/866.4 |
| 4213054 | 8/1992 | Japan | 73/866.4 |

*Primary Examiner*—Kenneth J. Ramsey
*Attorney, Agent, or Firm*—Wheeler & Kromholz

[57] ABSTRACT

Method to implant defects in a metallic component, for the retraining and qualification of operators and in non-destructive test techniques. This method is characterized by the implantation of non-homogenious material directly in the model item and to do so excavations are made that, following implantation of the defects, are filled by a welding process.

9 Claims, 2 Drawing Sheets

METHOD TO IMPLANT DEFECTS IN A METALLIC COMPONENT

The present invention refers to a method to construct a metallic model that contains defects of previously established type, size and location.

These metallic models are used for the training and qualification of personnel and in inspection techniques for non-destructive tests. The geometric form of the models is similar to the most representative of the metallic constructions to be inspected. Their weight may vary from a few kilos up to various tens of tons, with the material used being produced and thermally treated in a similar way to the piece represented.

Metallic components can suffer various types of defects (faults of continuity in the material) during their manufacturing process and/or during their working life, and these may be represented by some of the following three types:

Fine defect, consisting of a flat crack with very fine borders.

Thick defect in which a broken crack with damaged borders is found.

Volumetric defect, consisting of a hole in the metal.

The need to be able to detect any known defect by the use of ultrasonics, has been the object of regulations and is a standard that must be complied with by various national and international entities, particularly in the case of installations for nuclear power plants, whether the inspection is carried out during installation or during the time the plant is working. It was established that it must be possible to simulate the reactor core holder, having first placed a number of simulated defects, therein. Using the remains of a nuclear reactor the company owning this patent began to implant various defects in its core holder. Later the PISC program, promoted by the EEC, also planned the implantation of defects in real models. According to the directives for this program a series of models were made and sent all over the world for a period of approximately two years, remaining for some fifteen days in each analyzing center, which issued a report on the defects detected. At the end of the run, a study was made of the analyses issued by the different centers, to discover the degree of correctness or failure in their techniques. As a secondary consequence, it was found that this system also allowed an evaluation of different analysis systems used, determining the validity of each one.

Thus everyone agrees that in order to correctly study a defect, real models must be used that contain defects. The technique used to date to implant these defects was, as already indicated, developed in part by the company applying for this patent, and in part by other manufacturers, particularly European ones, that in the past began the manufacture of real models.

According to one of the techniques used up until now, cracks were made by placing two materials together and welding round the joint. When this weld was made the material contracted but because of the lack of penetration of the material a crack was left whose form could be varied according to the sides of the pieces joined together. In this technique it is very important that the edge of the crack be very fine in transversal section, since a greater or lesser opening of the crack is obtained according to the roughness of the two facing planes.

Fatigue cracks are very fine, particularly on their edge where they normally have a size of less than 0.02 mm. In order to obtain a defect of this type a test piece was prepared in which a hole was drilled that underwent controlled fatigue force under which the said drilled hole progresses and the crack advances to the desired point. With this process a defect of specific size is obtained when the test piece is out to the appropriate size.

Thus for either of the two methods described above a test piece was necessary, consisting of a cube or ball shaped piece in which the desired effect was obtained, either by the method of putting two pieces together or by placing controlled fatigue force on it. Finally, it was necessary to carry out a process to implant the test piece in the model that was finally to include the defect.

To implant the test piece in the model, a hole was made in the latter larger than the test piece so that access was possible to it from all directions. Later the test piece was placed in the desired position and finally all the remaining volume was completely closed by welding. The latter welding process must be carried out with great care to avoid the formation of later defects caused by the procedure itself. To carry out the implantation both sides of the test piece must be welded simultaneously to avoid stresses and deformation, which would cause possible displacements or rotations of the test piece that can cause the defect to move. Contractions also exist that can cause longitudinal displacement of the test piece when welding from inside outwards. In sum, very great uncertainty exists regarding the implantation process itself with reference to the possible definitive location of the defects and the creation of possible additional defects, and therefore this phase of the implantation process was extremely critical.

The method described here avoids the root of these problems since the defects are implanted directly on the model element in a predetermined place. To do this holes are cut in which the defect is created directly and later the hole created is refilled using a welding process.

The object of the present invention can better be understood with the aid of the following description based on a practical example of how a model is made containing examples of various types of defects. The said description is given with the aid of the attached plans, in which.

Figure 4:
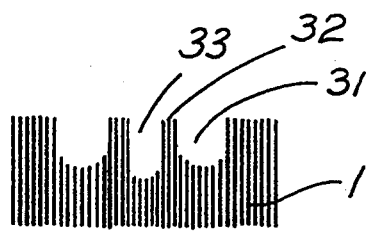
Figure 5:
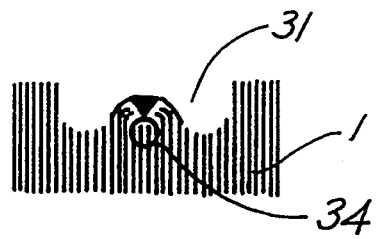
Figure 6:

FIGS. 4, 5 and 6 also show a schematic sectional view of the method used to implant a volumetric defect.

Figure 7:
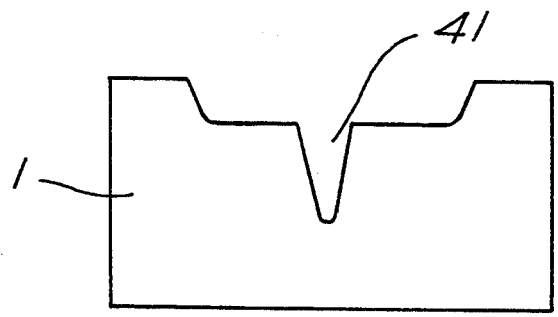
Figure 8:
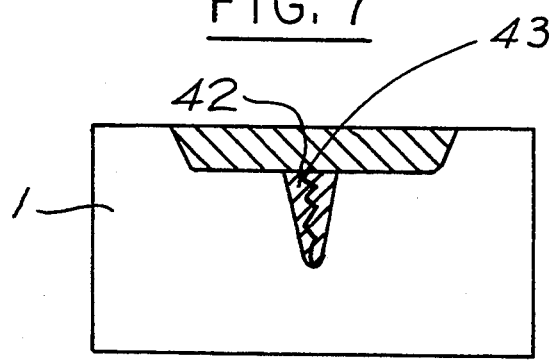

Lastly, FIGS. 7 and 8 represent a schematic view of the method used to implant a rough defect.

Figure 1:
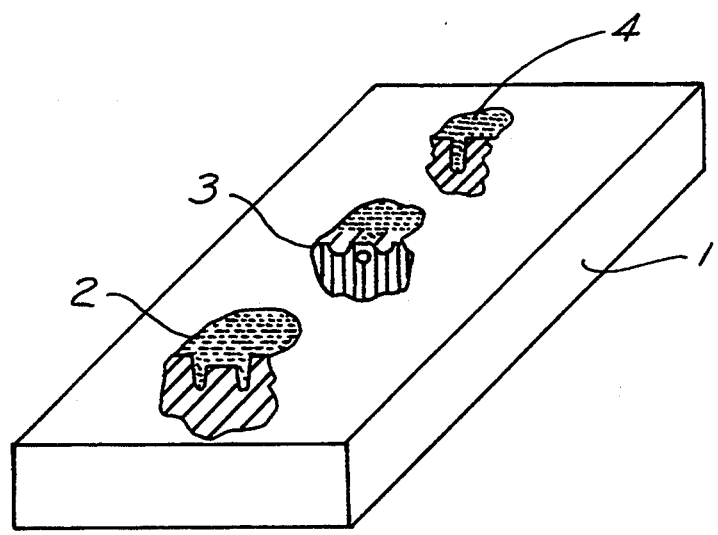
FIG. 1 shows a schematic view of a component in which the types of defects have been implanted.
Figure 2:
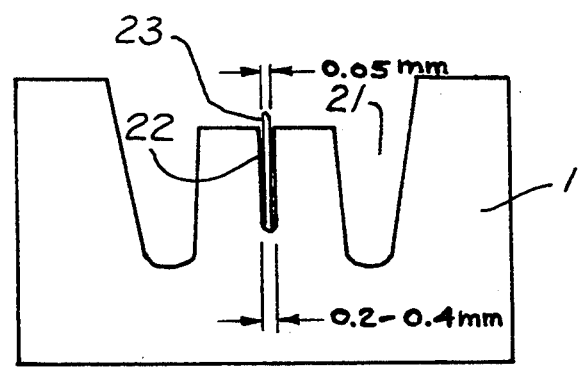
FIGS. 2 and 3 show a sectional view of a method for implanting a fine defect.
Figure 3:
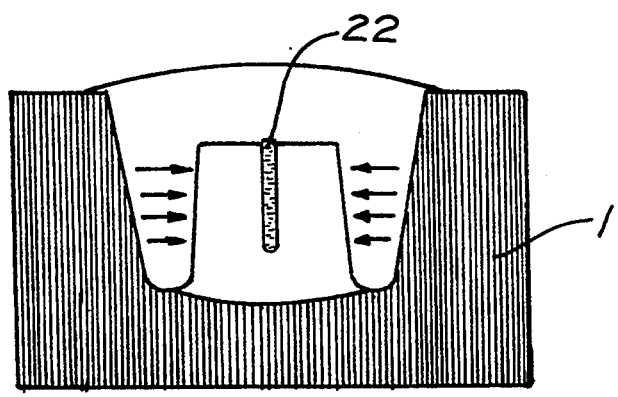

FIGS. 2 and 3 show the phases before and after the implantation of a fine defect (2) in a metallic model (1). First of all a recess (21) is prepared in the model (1), in the place and with the slope desired. During a later operation a drilling is made by electro-erosion in the place, shape and sizes required for the defect. The width of the bottom is as small as possible (0.2–0.4 mm). Inside the drilling (22) a refractory or ceramic covered element (23) is placed, with the smallest possible thickness (0.05 mm or less), in such a way that during the forging process described below the weld cannot enter between the two faces of the drilling, thus creating a very fine crack, particularly at its lower apex. The refractory element used can, for example, be flour, zirconium paint or mica.

The volume of metallic material containing the drilling and its surrounding area is heated to forging temperature (1100 degree C. for steel) and plastic deformation is carried out by impact/compression. Consequently the width of the drilling (22) is reduced to 0.05 mm or less, giving rise to a defect that responds to ultrasonics in a similar way to an actual fine crack. The groove initially prepared is filled by conventional arc welding with appropriate precautions to avoid deformation. During the welding process the drilling (22) may tend to open on the outside, but this does not cause any problem since fatigue cracks are normally of this type, with an important separation on the outside and extremely fine on the edge. The important thing in this case is to be able to detect by ultrasonics the depth to which this crack enters, taking as a reference the lower end of the same that, as already stated, must be less than 0.02 mm.

With the aid of FIGS. 4, 5 and 6, described below is the method for producing a volumetric defect (3). A recess (31) is tooled into the model (1) and has two fine lips (32) facing each other. In the central hole (33) placed between them a solid is introduced (34) of the desired shape and length; thereafter the lips (32) of base material are pressed down over this, as shown in FIG. 5, and then the area of the join of the lips is welded with low thermal TIG solder, and the whole area of the groove is filled in, as shown in the final FIG. 6.

Lastly, with the aid of FIGS. 7 and 8 the production procedure is described for a rough crack (4) on a model (1). The process also begins with the preparation of a recess (41) appropriately located and of exact size, so that exactly in the central axis of this recess (41) is the place where the required defect will be implanted. Using TIG arc welding and with the addition of filler material similar to the base material used, save that the sulphur content will be 0.3% approximately, and by depositing successive layers of thin cords (42) a longitudinal crack is obtained in each layer in the centre of each cord. The successive deposits of cords form a continuous and broken crack (43) with a height determined by the depth of the groove, while the length is obtained by making a longer crack than required and later repairing both ends.

Having sufficiently described the nature of the present invention and the manner of putting it into practice, we need only add that as a whole and in its parts, it is possible to make changes of shape, materials and layout, always providing these alterations do not substantially change the characteristics of the invention claimed below.

I claim:

1. A method for directly implanting a defect, of a type selected from any fine, thick or volumetric defect, into a model element, the method comprising the steps of:
    cutting a recess in the model element;
    placing the defect in the recess;
    deforming a portion of the recess to substantially cover the defect; and
    subsequently refilling the recess by a welding process.

2. A method for implanting a fine defect in a metallic component, the method comprising the steps of:
    cutting a recess in the metallic component;
    drilling a hole in the recess;
    placing a refractory element in the hole;
    forging the hole substantially, but not completely, closed; and
    filling the recess with a filler material.

3. A method for implanting a volumetric defect in a metallic component, the method comprising the steps of:
    cutting a recess in the metallic component, the recess having two lips facing each other;
    placing a solid in the recess;
    pressing the lips over the solid, the lips meeting at a joint;
    welding the joint; and
    filling the recess with a filler material.

4. A method for implanting a thick defect in a metallic component, the method comprising the steps of:
    cutting a recess in the metallic component, said recess having an axis;
    depositing successive thin layers of weld material along the axis of the recess to obtain a longitudinal crack in each layer; and
    subsequently refilling the recess by a welding process.

5. The method of claim 4 including the further step of:
    repairing the ends of the crack to a predetermined crack length.

6. A method for directly implanting a fine defect into a model element, the method comprising the steps of:
    cutting a recess in the model element;
    drilling a hole in the recess by electro-erosion of a size required by the defect;
    placing a refractory element having a small thickness in the hole;
    forging and deforming the hole by impact and compression to reduce, without closing, the hole; and
    subsequently refilling the recess by a welding process.

7. A method for directly implanting a volumetric defect into a model element, the method comprising the steps of:
    cutting a recess in the model element, the recess having two fine lips facing each other;
    placing a solid in the recess between the lips;
    pressing the lips over the solid, the lips meeting at a joint;
    welding the joint; and
    subsequently refilling said recess by a welding process.

8. A method for directly implanting a rough crack defect, the defect having a predetermined height, into a model element, the method comprising the steps of:
    cutting an elongated recess to a depth at least as deep as the predetermined defect height;
    said recess having an axis in the model element;
    welding successive thin layer of weld material along the axis to obtain a longitudinal crack in each layer; and
    subsequently refilling said recess by a welding process.

9. The method of claim 8 including the further step of:
    repairing the ends of the crack to a predetermined crack length.

* * * * *